United States Patent [19]

Hiroshi et al.

[11] Patent Number: 4,602,086

[45] Date of Patent: Jul. 22, 1986

[54] METHOD OF PRODUCING SOLUTION CONTAINING D-RIBOSE

[75] Inventors: Namikiri Hiroshi, Funabashi; Tobe Takeshi; Hattori Masahiko, both of Tokyo, all of Japan

[73] Assignee: Tokyo Tanabe Company, Limited, Tokyo, Japan

[21] Appl. No.: 659,272

[22] Filed: Oct. 10, 1984

[30] Foreign Application Priority Data

Oct. 13, 1983 [JP] Japan ................................ 58-189976
Nov. 29, 1983 [JP] Japan ................................ 58-223187

[51] Int. Cl.$^4$ ............................................. C07H 1/00
[52] U.S. Cl. ...................................... 536/125; 536/1.1
[58] Field of Search ......................... 536/1.1, 4.1, 125

[56] References Cited

U.S. PATENT DOCUMENTS 4,355,158 10/1982 Wolf et al. ........................... 536/1.1
4,360,669 11/1982 Schmidt et al. ....................... 127/29

*Primary Examiner*—Johnnie R. Brown
*Assistant Examiner*—Elli Peselev
*Attorney, Agent, or Firm*—McGlew and Tuttle

[57] ABSTRACT

A D-ribose-containing solution is produced in a high epimerization ratio, such as 60–94%, by epimerizing D-arabinose dissolved in an adequate solvent in the presence of a molybdic acid ion and a boric acid compound. The solution is useful as an inexpensive material on the industrial syntheses of vitamin $B_2$ or nucleic acids.

12 Claims, No Drawings

METHOD OF PRODUCING SOLUTION CONTAINING D-RIBOSE

FIELD AND BACKGROUND OF THE INVENTION

This invention relates to a method of producing a solution containing D-ribose by epimerizing a solution containing D-arabinose.

D-ribose is a compound which is important as a constituent of nucleic acid, or as a material for synthesizing vitamin $B_2$. It is known that D-ribose can be produced by extraction from natural matter, fermentation by a micro-organism, or chemical synthesis from furan or glucose. All of these methods, however, are complicated and have a low yield.

The production of D-ribose on an industrial basis has usually been carried out by a method comprising oxidizing D-glucose with oxygen in an aqueous alkali solution to form D-arabonic acid, separating it in the form of a calcium salt, heating it in an aqueous alkali solution for epimerization to form D-ribonic acid, separating it in the form of a metal salt, such as mercury or zinc salt, lactonizing it into D-ribonolactone, and reducing it with a sodium amalgam into D-ribose. The heating of D-arabonic acid in an aqueous alkali solution forms a mixture having an equilibrium D-arabonic acid to D-ribonic acid ratio of 70:30. It is impossible to obtain any D-ribonic acid proportion exceeding 30%. This method is inconvenient to the use of a large quantity of mercury for amalgam reduction.

Bilik et al. reported the epimerizability of various saccharides in an aqueous solution in the presence of a molybdic acid catalyst, including, for example, the epimerizability of about 33% of L-arabinose into L-ribose (Czechoslovak Pat. No. 149,472; Chemical Abstracts, 81, 78189K). A method based on this report was proposed, and comprises oxidizing D-gluconic acid, instead of converting it to D-arabonic acid and D-ribonic acid, converting D-gluconic acid to D-arabinose with hypochlorous acid, and epimerizing D-arabinose to D-ribose in an aqueous solution in the presence of a molybdic acid VI compound as a catalyst (Japanese Laid-Open Patent Specification No. 164699/1980). This method achieves an epimerization ratio (ratio of ribose in an equilibrium mixture) of only about 25%, but is superior to the method hereinbefore described in that it does not use mercury, and requires only a fewer steps. In order to facilitate the separation of molybdic acid from an aqueous solution upon completion of an epimerization reaction using molybdic acid (molybdic acid VI compound) as a catalyst, there has been proposed the use of an ion exchange resin carrying molybdic acid instead of molybdic acid (Japanese Patent Publication No. 40700/1981), or the use of an ion exchange fiber carrying molybdic acid (Japanese Laid-Open Patent Specification No. 76894/1980 disclosing an epimerization ratio of 30.6% from D-arabinose to D-ribose, and Japanese Laid-Open Patent Specification No. 54197/1982 disclosing an epimerization ratio of 27.2% from D-arabinose to D-ribose).

It is known that the heating of L-arabinose in dimethylformamide in the presence of dioxobis(2,4-pentanedionoto-0, O'-)molybdenum (VI) achieves epimerization of 36% thereof to L-ribose [Abe et al.: Chemical and Pharmaceutical Bulletin, 28, 1324 (1980)].

SUMMARY OF THE INVENTION

Under these circumstances, the inventors of this invention have studied the possibility of producing D-ribose on an industrial basis at a lower cost and with an improved epimerization ratio. As a result, we have found that an improved epimerization ratio up to at least about 60% can be obtained if a boric acid compound is added to a known reaction system for producing D-ribose by epimerizing D-arabinose in an aqueous solution using a molybdic acid ion as a catalyst. As a result of further research, we have found that an improved epimerization ratio up to 94% can be realized if an organic solvent is used instead of water.

In accordance with this invention, there is provided a method of producing a solution containing D-ribose from a solution containing D-arabinose, which comprises epimerizing D-arabinose dissolved in a solvent such as a solvent selected from the group consisting of water, an organic solvent and an organic solvent containing water, to D-ribose, in the presence of a molybdic acid ion and a boric acid compound.

DESCRIPTION OF THE PREFERRED EMBODIMENTS

According to this invention, it is possible to use any solvent dissolving D-arabinose and a boric acid compound, for example, water, an organic solvent such as methanol, ethanol, n-propanol, isopropanol, n-butanol, isobutanol, sec-butanol, t-butanol, n-amyl alcohol, iso-amyl alcohol, sec-amyl alcohol, n-hexanol, methylamyl alcohol, 2-ethyl-hexanol, cyclohexanol, ethylene glycol, diethylene glycol, propylene glycol, ethylene glycol monomethyl ether (methyl cellosolve), diethylene glycol monoethyl ether (carbitol) or diethylene glycol monomethyl ether (methyl carbitol), acetone, ethyl-acetone, methyl ethyl ketone, 1,4-dioxane, pyridine, α-picoline, 2,6-lutidine, acetonitrile, N,N-dimethylformamide (DMF), N,N-dimethylacetoamide (DMA) or dimethylsulfoxide (DMSO), or an above-mentioned organic solvent containing water.

If water is used as the solvent, it is possible to use it in a quantity not exceeding 10 times (w/w), preferably not exceeding one time, and more preferably 0.5 to 1 time as much as D-arabinose. If an organic solvent is used, it is suitable to use not more than 10 times (w/v) as much of the solvent as D-arabinose, and preferably 0.5 to 3 times as much. Although it is possible to use an organic solvent containing water, it is preferable to use an organic solvent having a low water content or not containing water, since a higher water content gives a lower epimerization ratio.

It is possible to use as a source of supply of a molybdic acid ion, a molybdic acid (VI) compound of the type used for the epimerization of saccharides, for example, molybdic acid, ammonium molybdate, potassium molybdate, sodium molybdate, calcium molybdate or acetylacetone molybdate. It is also possible to use molybdic acid carried on an ion exchange resin or fiber. It is suitable to use a molybdic acid ion in the quantity of 1 to 10% (w/w), preferably 5 to 10%, of D-arabinose.

In the event water is used as the solvent, it is possible to use any water-soluble boric acid compound, for example, boric acid, boron oxide or methyl borate, or a borate such as ammonium, potassium or sodium borate. If an organic solvent not containing water is used, it is preferable to use boric acid. If an organic solvent containing water is used, it is suitable to use boric acid, boron oxide or methyl or ethyl borate, or a borate, such as ammonium or potassium borate. It is suitable to use the boric acid compound in a molar quantity which is at least 0.5 times, or preferably 1.5 to times, as large as that of D-arabinose.

If an aqueous solution containing D-arabinose, a molybdic acid ion and a borate is used for the reaction, its pH is adjusted to a level of about 3 to 3.5. If an organic solvent containing or not containing water and a borate are used, it is first necessary to hydrolyze the borate with an organic or inorganic acid to form boric acid.

The reaction may be carried out under reflux if a solvent having a boiling point less than 90° C. is used, or at a temperature of 90° C. to 95° C. if the solvent has a boiling point of 90° C. or above. The reaction may be carried out at atmospheric pressure. The reaction time may be from 30 to 60 minutes. If the solution is cooled to ambient temperature after the reaction, a part of boric acid is precipitated. The removal of the precipitate reduces the load of after-treatment.

The D-ribose-containing solution prepared in accordance with this invention contains in addition to D-ribose, D-arabinose, very small quantities of D-xylose and D-lyxose, a molybdic acid ion and borate. It may further contain ions and by-products arising from the reaction solvent and materials used.

If an organic solvent containing or not containing water is used, it is possible to remove after the removal of the solvent the molybdic acid catalyst by a known method, such as ion exchange or electric dialysis. It is, then, possible to remove boric acid or a salt thereof by a known method, for example, by adding a lower alkyl alcohol, such as methanol, and repeating concentration to dryness, or by treating the solution with an ion exchange resin (weakly basic).

A known method employing, for example, a cation exchange resin loaded with a calcium or barium ion can be used to separate D-ribose from the solution from which the catalyst and boric acid or the salt thereof have been removed. This ion exchange resin treatment may be carried out after the solution has been concentrated and extracted from ethanol for the separation by precipitation of the greater part of D-arabinose, if required.

This invention has the advantage of achieving a maximum epimerization ratio of about 94% and a low degree of D-xylose and D-lyxose formation.

It is possible for example, to obtain pure N-D-ribityl-3,4-xylidine from the D-ribose-containing solution prepared in accordance with this invention and having a high D-ribose content, which is preferably at least 60%, if the solution from which only the catalyst has been removed is catalytically reduced in the presence of 4-nitro-0-xylene or 3,4-xylidine, and if the resulting mixture is crystallized. As the addition of a solvent, such as methanol, to the solution for its catalytic reduction causes precipitation of a part of boric acid, it is possible to carry out the catalytic reduction after removing the precipitated boric acid. It is possible to obtain vitamin $B_2$ if N-D-ribityl-3,4-xylidine is subjected to a coupling reaction with a diazonium salt solution to synthesize 1-D-ribitylamino-3,4-dimethyl-6-phenylazobenzene, and if the synthesized product is condensed with barbituric acid.

The analysis of saccharides in the following examples was performed by reducing the saccharides in a sample solution with sodium borohydride to form the corresponding sugaralcohol, acetylating it with anhydrous trifluoroacetic acid and subjecting the acetylated product to gas chromatography.

EXAMPLE 1

A solution obtained by adding 15 ml of water, 1.4 g of ammonium molybdate and 18.3 g of boric acid to 15 g of D-arabinose was reacted by heating at 95° C. for 30 minutes under stirring. The reacted solution was cooled, and the resulting precipitate was removed by filtration. After the catalyst had been removed from the solution by treatment with an ion exchange body (strongly acid and weakly basic), the solution was concentrated to about a half volume to yield 32 g of a transparent solution. The solution was found to contain the following saccharides:
D-ribose: 68.1%
D-arabinose: 29.9%
D-xylose and D-lyxose: 2.0%

EXAMPLE 2

A solution obtained by adding 100 ml of water, 10.5 g of molybdic acid (80%) and 762 g of sodium borate $(Na_2B_4O_7.10H_2O)$ to 100 g of D-arabinose was heated at 90° C. for an hour under stirring after its pH value had been adjusted to 3.2. The precipitate was removed from the solution by filtration, and molybdic acid was removed by a weakly basic anion exchange resin. After the solution had been desalted by a cation exchange resin, boric acid was removed from the solution by adding methanol and repeating concentration to dryness at a reduced pressure, whereby there were obtained 123 g of a transparent solution. The solution was found to contain the following saccharides:
D-ribose: 66.9%
D-arabinose: 31.3%
D-xylose and D-lyxose: 1.8%

EXAMPLE 3

A solution obtained by adding 80 ml of water, 10.5 g of sodium molybdate and 82.3 g of boric acid to 100 g of D-arabinose was reacted at 95° C. for 30 minutes under stirring. The reacted solution was cooled, and the precipitate was removed by filtration. The solution was treated with a chelate resin (CR-10; product of MITSUBISHI CHEMICAL INDUSTRIAL CO., LTD.) for the removal of molybdic acid, and desalted by a strongly acidic cation exchange resin (SK-1B; product of MITSUBISHI CHEMICAL INDUSTRIAL CO., LTD.). The solution was concentrated to dryness at a reduced pressure, and 100 ml of methanol were added to the solution. The residual crystals were separated by filtration, and washed carefully with methanol. The filtrate and the washing solution were combined and distilled at a reduced pressure to remove methanol. Then, 100 ml of water were addedto the residue and the resulting solution was treated with an ion exchange resin to remove the boric acid ions completely. The solution was concentrated at a reduced pressure to yield about 153 g of a transparent solution. The solution was found to contain the following saccharides:
D-ribose: 65.6%
D-arabinose: 32.1%
D-xylose and D-lyxose: 2.3%

EXAMPLE 4

A solution obtained by adding 15 ml of water, 1.8 g of ammonium molybdate and 27.8 g of boron oxide to 20 g of D-arabinose was heated at 92° C. for 30 minutes under stirring after its pH had been adjusted to 3.2 with acetic acid. The reacted solution was cooled to ambient temperature, and the precipitate was removed by filtration. The catalyst was removed by ion exchange resins (strongly acid and weakly basic). The greater part of boric acid was removed from the solution by its concentration at a reduced pressure and the addition of methanol thereto. The remaining boric acid was completely removed from the solution by its treatment with an ion exchange resin (Amberlite IRA-743 of ORGANO CO., LTD.). The solution was found to contain the following saccharides:

D-ribose: 69.8%
D-arabinose: 27.8%
D-xylose and D-lyxose: 2.4%

The solution was passed through a column dharged with a calcium type cation exchange resin at a rate of 0.8 ml/min., and divided by a fraction collector. The fractions of D-ribose were collected, concentrated at a reduced pressure and treated with ethanol to obtain 7.8 g of D-ribose crystal having a melting point of 86.4° C. and a purity of 100% as ascertained by gas chromatography.

EXAMPLE 5

A solution was obtained by dissolving 1.5 g of D-arabinose in 3 ml of water and adding 150 mg of ammonium molybdate and 1.0 g of boric acid. After sulfuric acid had been added to the solution to adjust its pH value to 3.3, it was heated at 95° C. for 30 minutes under stirring. The reacted solution was cooled and the precipitate was removed by filtration. After the catalyst had been removed by an ion exchange body (strongly acid and weakly basic), the filtrate was concentrated to about a half volume to yield 2.4 g of a transparent solution. The solution was found to contain the following saccharides:

D-ribose: 59.8%
D-arabinose: 37.4%
D-xylose and D-lyxose: 2.8%

EXAMPLE 6

A solution obtained by dissolving 15.0 g of D-arabinose in 15 ml of water and adding 2.2 g of potassium molybdate and 15 g of boric acid was heated at 90° C. for 60 minutes under stirring. The reacted solution was cooled to ambient temperature and the precipitate was removed by filtration. After the catalyst had been removed by ion exchange resins (strongly acid and weakly basic), the filtrate was concentrated at a reduced pressure, and the addition of 10 ml of methanol resulted in the precipitation of 12 g of boric acid. It was removed by filtration and the filtrate was found to contain the following saccharides:

D-ribose: 67.8%
D-arabinose: 30.1%
D-xylose and D-lyxose: 2.1%

The solution for example was then placed in an autoclave, and 8.7 g of 3, 4-xylidine, 50 ml of methanol, 30 g of Raney nickel (containing water) and 1.3 g of sodium acetate were added to the solution. The autoclave was charged with hydrogen up to a pressure of 50 kg/cm$^2$, and the solution was heated to 60° C. under stirring and reacted for 80 minutes. The Raney nickel catalyst was removed from the reaction solution by filtration. The filtrate was concentrated into about 100 ml and cooled slowly, resulting in the precipitation of crystal. After the solution had been left in a refrigerator a whole day and night, the crystal was collected by filtration, washed with 50 ml of cold water and dried to yield 12.1 g of N-D-ribityl-3,4-xylidine having a melting point of 138° C. to 140° C.

EXAMPLE 7

A solution obtained by adding 15 ml of ethanol, 1.2 g of ammonium molybdate and 18.5 g of boric acid to 15.0 g of D-arabinose was heated at 78° C. for 60 minutes under stirring. Both D-arabinose and boric acid, which were not dissolved very well at ordinary room temperature, could gradually be dissolved when heated. The reacted solution was cooled and the precipitate was removed by filtration. The solvent was removed by distillation at a reduced pressure. After 30 ml of water had been added to the distillation residue, it was treated with a weakly basic anion exchange resin (Amberlite IRA-99 of ORGANO CO., LTD.) for the removal of molybdic acid. The solution was, then, treated with a weakly basic anion exchange resin (Amberlite IRA-743 of ORGANO CO., LTD.) for the removal of boric acid ions, and concentrated at a reduced pressure until its saccharide content was about 50%. The solution was found to contain the following saccharides:

D-ribose: 94.0%
D-arabinose: 4.2%
D-xylose and D-lyxose: 1.8%

The solution was fed at a rate of 120 ml per hour into a column filled with a calcium type cation exchange resin (MK-31 of MITSUBISHICHEMICAL INDUSTRIAL CO., LTD.), and divided by a fraction collector. The fractions of D-ribose were collected and concentrated at a reduced pressure. After ethanol had been added, they were left a whole day and night to obtain 12.6 g of D-ribose crystal having a melting point of 84° C. to 85° C. and a specific rotation $[\alpha]_D^{24}$ of $-18.4°$ (C=1, H$_2$O).

EXAMPLE 8

A solution was prepared by adding 37.5 ml of 5% water-containing ethylene glycol, 2.3 g of molybdic acid (80%) and 76.3 g of sodium borate (Na$_2$B$_4$O$_7$.10-H$_2$O), and sulfuric acid was added to the solution to adjust its pH to 3.5. The solution was heated at 90° C. for 60 minutes under stirring, and cooled. After 15 ml of ethylene glycol had been added to the solution, it was left a whole night, and the precipitate was removed by filtration. The solvent was removed from the filtrate by distillation at a reduced pressure, and 100 ml of methanol were added to the distillation residue to remove the greater part of boric acid and sodium sulfate by filtration. These procedures were repeated three times. Then, methanol was removed from the solution by distillation, and after 30 ml of water had been added to the solution, it was treated with a weakly basic anion exchange resin of the MR type (IRA-743 of ORGANO CO., LTD.) for the removal of molybdic acid ions. The solution was further treated with Diaion CRB02 (product of MITSUBISHI CHEMICAL INDUSTRIAL CO., LTD.) for the removal of boric acid, and concentrated until its saccharide content was about 50%. The solution was found to contain the following saccharides:

D-ribose: 89.3%
D-arabinose: 7.8%
D-xylose and D-lyxose: 2.9%

The solution was passed through a boric acid type anion exchange resin (Dowex 1-X4; 100 to 200 mesh) at a rate of 2.0 ml/min. and fractionated by a fraction collector. The fractions of D-ribose were collected and concentrated at a reduced pressure. Methanol was added to remove boric acid. After 35 ml of a solution containing ethanol and acetone at a ratio of 2:1 had been added to the solution, it was left a whole night in a cold place to obtain 11.8 g of D-ribose crystal having a melting point of 84° C. and a specific rotation $]\alpha]_D^{24}$ of −18.6° (C=1, H$_2$O).

EXAMPLE 9

A solution obtained by adding 20 ml of isopropanol, 2.2 g of potassium molybdate and 25.0 g of boric acid to 20 g of D-arabinose was heated at 82.3° C. for 40 minutes under stirring. After 20 ml of isopropanol had further been added to the solution, it was left a whole night in a cold place for the partial precipitation of boric acid. After the precipitate had been removed by filtration and the solvent by distillation at a reduced pressure, water was added for the removal of molybdic acid by electric dialysis. The solution was, then, treated with an ion exchange body (Diaion CRBO2 of MITSUBISHI CHEMICAL INDUSTRIAL CO., LTD.) for the removal of boric acid, and concentrated at a reduced pressure until its saccharide content was about 50%. The solution was found to contain the following saccharides:
D-ribose: 91.9%
D-arabinose: 6.9%
D-xylose and D-lyxose: 1.0%

The procedures of EXAMPLE 7 were, then, repeated to obtain 16.3 g of D-ribose crystal having a melting point of 84° C. to 85° C. and a specific rotation $[\alpha]_D^{24}$ of −18.3° (C=1, H$_2$O).

EXAMPLE 10

A solution obtained by adding 15 ml of acetone, 2.5 g of acetylacetone molybdate [MoO$_2$(CH$_2$COCH$_2$COCH$_3$)$_2$] and 12.4 g of boric acid to 15.0 g of D-arabinose was refluxed for 40 minutes under stirring. After the solvent had been removed by distillation at a reduced pressure, 60 ml of methanol were added to the distillation residue and the undissolved matter was removed. After methanol had been removed by distillation, 30 ml of water were added and the solution was treated with a weakly basic anion exchange resin (Amberlite IRA-99 and IRA-743 of ORGANO CO., LTD.) for the removal of molybdic acid and boric acid ions. The solution was concentrated until its saccharide content was about 50%. The solution was found to contain the following saccharides:
D-ribose: 90.5%
D-arabinose: 7.7%
D-xylose and D-lyxose: 1.8%

The solution was subjected to column chromatography on a calcium-loaded ion exchange resin (Diaion MK-31 of MITSUBISHI CHEMICAL INDUSTRIAL CO., LTD.). The fractions of D-ribose were collected and concentrated. After a solution containing ethanol and acetone at a ratio of 2:1 had been added, the solution was left a whole night in a refrigerator to obtain 12.1 g of D-ribose crystal having a melting point of 83° C. to 84° C. and a specific rotation $[\alpha]_D^{24}$ of −18.4° (C=1,H$_2$O.

EXAMPLE 11

A solution was prepared by adding 45 ml of 10% water-containing isopropanol, 31.0 g of methyl borate and 1.2 g of ammonium molybdate to 15 g of D-arabinose, and 50% sulfuric acid was added to the solution to adjust its pH to 3.3. The solution was reacted under reflux for 60 minutes. The reacted solution was cooled slowly, and the precipitate was removed by filtration. The solvent was removed by distillation at a reduced pressure. The solution was treated with a weakly basic anion exchange resin (Amberlite IRA-99 and IRA-743 of ORGANO CO., LTD.) for the removal of molybdic and boric acid ions. Then, the solution was concentrated until its saccharide content was about 50%. The analysis of the saccharides in the solution was as follows:
D-ribose: 89.6%
D-arabinose: 8.3%
D-xylose and D-lyxose: 2.1%

The solution was passed through a calcium type cation exchange resin (MK-31 of MITSUBISHI CHEMICAL INDUSTRIAL CO., LTD.) charged in column. The fractions of D-ribose were collected and concentrated. After 50 ml of a solution containing ethanol and acetone at a ratio of 2:1 had been added, the solution was left a whole night in a refrigerator to obtain 12.0 g of D-ribose crystal having a melting point of 86° C. and a specific rotation $[\alpha]_D^{24}$ of −18.7° (C=1, H$_2$O).

EXAMPLE 12

A solution obtained by adding 18 ml of n-propanol, 1.5 g of ammonium molybdate and 23.0 g of boric acid to 20 g of D-arabinose was heated at 90° C. for 60 minutes under stirring. The reacted solution was cooled, and after 20 ml of n-propanol had been added, the solution was left in a cold place for the partial precipitation of boric acid. After the precipitate had been removed by filtration, the procedures of EXAMPLE 7 were repeated for the treatment of the solution with weakly basic anion exchange resins to remove molybdic acid and boric acid and for the concentration of the solution until its saccharide content was about 50%. The analysis of the saccharides in the solution was as follows:
D-ribose: 91.3%
D-arabinose: 7.3%
D-xylose and D-lyxose: 1.4%

The solution was found to contain 53.5% of reduced saccharides. An autoclave was charged with 500 ml of the solution and 137 ml of methanol, 16.3 g of 3,4-xylidine, 11.7 g of Raney nickel (containing water) and 0.5 g of sodium acetate. The autoclave was filled with hydrogen up to a pressure of 40 kg/cm$^2$. The solution was heated to 60° C. under stirring and reacted for 80 minutes. The Raney nickel catalyst was removed from the reacted solution by filtration. The filtrate was concentrated to about 200 ml and cooled slowly for the precipitation of crystal. The crystal was separated by filtration and recrystallized twice from a water-methanol mixture containing 50% of methanol to yield 24.8 g of N-D-ribityl-3,4-xylidine having a melting point of 145° C. and a specific rotation $[\alpha]_D^{24}$ of −21.8° (C=1, H$_2$O).

EXAMPLE 13

A solution obtained by adding 20 ml of diethylene glycol monoethyl ether (carbitol), 1.5 g of ammonium molybdate and 23.0 g of boric acid to 20 g of D-arabinose was heated at 92° C. for 80 minutes under stirring. After 60 ml of water had been added to the reacted solution, the solvent was removed therefrom by distillation at a reduced pressure. The solution was dried at a reduced pressure, and 150 ml of methanol were added thereto. After the resulting precipitate had been removed by filtration, methanol was removed by distillation and 50 ml of water were added. The solution was passed through a weakly basic anion exchange resin (Amberlite IRA-99 of ORGANO CO., LTD.) for the removal of molybdic acid. The solution was concentrated at a reduced pressure to about 50%. The analysis of the saccharides in the solution was as follows:

D-ribose: 92.8%
D-arabinose: 5.3%
D-xylose and D-lyxose: 1.9%

The solution in the quantity of 34.6 g was found to contain 54.6% of reduced saccharides. Then, for example, an autoclave was charged with 500 ml of the solution and 135 ml of methanol, 15.8 g of 3,4-xylidine, 11.4 g of Raneyl nickel (containing water) and 0.5 g of sodium acetate. The autoclave was filled with hydrogen up to a pressure of 40 kg/cm$^2$. The solution was heated to 60° C. under stirring and reacted for 80 minutes. The Raney nickel catalyst was removed from the reacted solution by filtration. The filtrate was concentrated to about 200 ml and cooled slowly for the precipitation of crystal. The crystal was separated by filtration and recrystallized from 50% methanol to yield 25.1 g of N-D-ribityl-3,4-xylidine having a melting point of 142° C. to 143° C. Its elemental analysis ($C_{13}H_{21}NO_4$) was as follows: Values theoretically obtained: C: 61.15%; H: 8.29%; O: 25.07%; N: 5.49%.

Values as actually determined: C: 61.1%; H: 8.1%; O: 25.2%; N: 5.4%.

EXAMPLE 14

A solution obtained by adding 15 ml of n-hexanol, 3.2 g of acetylacetone molybdate [$Mo)_2(CH_2COCH_2COCH_3)_2$] and 15.4 g of boric acid to 15 g of D-arabinose was stirred at 90° C. for 60 minutes. Water was added to the reacted solution and the solvent was removed by azeotropic distillation at a reduced pressure. Molybdic acid and boric acid were removed from the solution by electric dialysis. The solution was concentrated until its saccharide content was about 50%. The analysis of the saccharides in the solution was as follows:

D-ribose: 91.7%
D-arabinose: 6.8%
D-xylose and D-lyxose: 1.5%

The solution in the quantity of 27.8 g was found to contain 50.2% of reduced saccharides. The procedures of EXAMPLE 7 were repeated to produce from 500 ml of the solution 16.8 g of N-D-ribityl-3,4-xylidine having a melting point of 145° C. and a specific rotation $[\alpha]_D^{24}$ of $-21.8°$ (C=0.4, methanol).

What is claimed is:

1. A method of producing a solution containing D-ribose from a solution containing D-arabinose, which comprises epimerizing D-arabinose dissolved in a solvent to D-ribose, in the conjoint dissolved presence of a molybdic acid ion and a boric acid compound.

2. A method as set forth in claim 1, wherein the solvent is selected from the group consisting of water, an organic solvent and an organic solvent containing water.

3. A method as set forth in claim 2, wherein the organic solvent is selected from the group consisting of ethanol, n-propanol, isopropanol, n-hexanol, ethylene glycol, diethylene glycol monoethyl ether and acetone.

4. A method as set forth in claim 1, wherein a molybdic acid ion is employed in the quantity of 1 to 10%(w/w) of D-arabinose.

5. A method as set forth in claim 4, wherein a source of supply of the molybdic acid ion is selected from the group consisting of molybdic acid, ammonium molybdate, potassium molybdate, sodium molybdate and acetylacetone molybdate.

6. A method as set forth in claim 1, wherein a boric acid compound is employed in a molar quantity which is at least 0.5 times as large as that of D-arabinose.

7. A method as set forth in claim 6, wherein the boric acid compound is selected from the group consisting of boric acid, boron oxide, methyl borate and sodium borate.

8. A method as set forth in claim 1, wherein the epimerization ratio of D-arabinose to D-ribose is from 60% to 94%.

9. A method of producing a solution containing D-ribose from a solution containing D-arabinose, which comprises epimerizing D-arabinose dissolved in a solvent to D-ribose, in the conjoint presence of a molybdic acid ion and a boric acid compound also dissolved in said solvent, and sufficiently to achieve an epimerization ratio of the D-arabinose to D-ribose of at least about 89.3% in the resulting solution, said solvent being selected from the group consisting of an organic solvent and an organic solvent containing water.

10. Method of producing a solution containing D-ribose from a solution containing D-arabinose, which comprises epimerizing D-arabinose dissolved in a solvent to D-ribose, in the conjoint presence of a molybdic acid ion and a boric acid compound also dissolved in said solvent, and sufficiently to achieve an epimerization ratio of the D-arabinose to D-ribose of at least about 89.3% in the resulting solution, said solvent being selected from the group consisting of an organic solvent and an organic solvent containing water, and said boric acid compound being employed in a molar quantity which is at least 0.5 times as large as that of the D-arabinose.

11. Method of claim 10, wherein a molybdic acid ion is employed in the quantity of 1 to 10% (w/w) of the D-arabinose.

12. Method of claim 11, wherein the organic solvent is selected from the group consisting of ethanol, n-propanol, isopropanol, n-hexanol, ethylene glycol, diethylene glycol monoethyl ether and acetone, wherein a source of supply of the molybic acid ion is selected from the group consisting of molybdic acid, ammonium molybdate, potassium molybdate, sodium molybdate and acetylacetone molybdate, and wherein the boric acid compound is selected from the group consisting of boric acid, boron oxide, methyl borate and sodium borate.

* * * * *